US00PP13909P29

(12) United States Plant Patent
Fruehwirth

(10) Patent No.: US PP13,909 P2
(45) Date of Patent: Jun. 24, 2003

(54) POINSETTIA PLANT NAMED 'ECKAIMON'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/087,973

(22) Filed: Mar. 4, 2002

(51) Int. Cl.[7] ..... A01H 5/00

(52) U.S. Cl. ..... Plt./304

(58) Field of Search ..... Plt./304, 305, 303

(56) References Cited

PUBLICATIONS

UPOV–ROM GTITM Computer Database 2002/05, GTI Jouve Retrieval Software, Citation for Euphorbia 'Eckaimon'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Poinsettia plant named 'Eckaimon', characterized by its ball-shaped inflorescences with recurved pale yellow-colored flower bracts; recurved dark green-colored leaves; uniform plant habit; early flowering; and excellent postproduction longevity.

1 Drawing Sheet

BOTANICAL CLASSIFICATION/CULTIVAR DESIGNATION

*Euphorbia pulcherrima* Willd. cultivar Eckaimon.

BACKGROUND OF THE INVENTION

The present Invention relates to a new and distinct cultivar of Poinsettia plant, botanically known as *Euphorbia pulcherrima* Willd., and hereinafter referred to by the name 'Eckaimon'.

The new Poinsettia a product of a planned breeding program conducted by the Inventor in Encinitas, Calif. The objective of the breeding program is to create new Poinsettia cultivars having strong stems, reflexed flower bracts with desirable colors, uniform plant habit and excellent post-production longevity.

The new Poinsettia originated from a cross made by the Inventor of a proprietary selection of *Euphorbia pulcherrima* Willd. identified as code number M-29, not patented, as the female, or seed, parent, with a proprietary selection of *Euphorbia pulcherrima* Willd. identified as F-14, not patented, as the male, or pollen, parent. The cultivar Eckaimon was discovered and selected by the Inventor as a flowering plant within the progeny of the stated cross in a controlled environment in Encinitas, Calif., in December, 1994. The selection of this plant was based on its strong stems and reflexed flower bracts.

Asexual reproduction of the new Poinsettia by terminal cuttings propagated in a controlled environment in Encinitas, Calif., since 1995, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckaimon'. These characteristics in combination distinguish 'Eckaimon' as a new and distinct cultivar:

1. Ball-shaped inflorescences with recurved pale yellow-colored flower bracts.
2. Recurved dark green-colored leaves.
3. Uniform plant habit.
4. Strong erect stems.
5. Early flowering; natural season flower maturity date is early December for plants grown in Encinitas, Calif.; response time, about 9 weeks.
6. Excellent post-production longevity.

Plants of the new Poinsettia differ primarily from plants of the female parent, the selection M-29, in flower bract coloration as plants of the female parent have light red-colored flower bracts. In addition, plants of the new Poinsettia have stronger stems than plants of the female selection.

Plants of the new Poinsettia differ primarily from plants of the male parent, the selection F-14, in flower bract coloration and orientation as plants of the male parent have dark red-colored flower bracts that are flat and not reflexed. In addition, plants of the new Poinsettia have stronger stems than plants of the male selection.

Plants of the new Poinsettia can also be compared to plants of the cultivar Windark, disclosed in U.S. Plant Pat. No. 12,546. In side-by-side comparisons conducted in Encinitas, Calif., plants of the new Poinsettia differed primarily from plants of the cultivar Windark in the following characteristics:

1. Plants of the new Poinsettia had lighter green-colored leaves than plants of the cultivar Windark.
2. Flower bracts of plants of the new Poinsettia were pale yellow in color whereas flower bracts of plants of the cultivar Windark were dark red in color.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a side perspective view of a typical flowering plant of 'Eckaimon' grown in a 16.5-cm container.

The photograph at bottom of the sheet is a close-up view of typical leaves and flower bracts of 'Eckaimon'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polycarbonate-covered greenhouse with day temperatures about 24 to 29° C., night temperatures about 19° C., and light levels about 4,000 foot-candles. Single plants were grown in 16.5-cm pots and pinched once. Plants were flowered under natural season short day/long night conditions. Plants were about 18 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Eckaimon.

Parentage:

*Female parent.*—Proprietary selection of *Euphorbia pulcherrima* Willd. identified as code number M-29, not patented.

*Male parent.*—Proprietary selection of *Euphorbia pulcherrima* Willd. identified as code number F-14, not patented.

Propagation:

*Type cutting.*—Terminal cuttings.

*Time to initiate roots.*—About 10 days at 20 to 22° C.

*Time to develop roots.*—About 28 days at 24° C.

*Root description.*—Thick, fibrous and freely-branching.

Plant description:

*Plant form.*—Inverted triangle; thick, strong and erect stems.

*Growth habit.*—Upright and uniform plant habit. Moderately vigorous to vigorous.

*Plant height.*—About 30 cm.

*Plant diameter or spread.*—About 26 cm.

*Lateral branch description.*—Quantity: About three lateral branches develop after pinching. Length: About 24 cm. Diameter: Thick, about 8 mm. Internode length: About 2.75 cm. Strength: Strong, stiff. Texture: Smooth; glabrous. Color: Slightly darker than 144A.

*Foliage description.*—Arrangement: Alternate, single. Quantity of leaves per lateral branch: About nine. Length: About 9 cm. Width: About 10 cm. Shape: Roughly ovate. Apex: Acuminate. Base: Cordate. Margin: Entire with irregular lobing, typically about three to five lobes. Venation pattern: Pinnate. Texture: Upper surface: Glabrous. Lower surface: Slightly pubescent. Surface: Slightly rugose. Orientation: Recurved. Color: Young foliage, upper surface: Closest to 137A. Young foliage, lower surface: 138A. Fully expanded foliage, upper surface: 147A. Fully expanded foliage, lower surface: 137B. Venation, upper surface: 147C. Venation, lower surface: 147D. Petiole: Length: About 2.3 cm. Diameter: About 3.5 mm. Texture, upper and lower surfaces: Smooth; glabrous. Color: 144A.

Inflorescence description:

*Inflorescence type and habit.*—Inflorescences are compound corymbs of cyathia with colored flower bracts subtending the cyathia. One inflorescence per lateral branch. Flower bracts recurved, inflorescences ball-shaped. Flowers are not fragrant. Flowers persistent.

*Natural flowering season.*—Autumn/winter in Northern Hemisphere. Flower initiation and development is induced under long nyctoperiod conditions. Early flowering; response time, about 9 weeks; natural season flower maturity date is early December for plants grown in Encinitas, Calif.

*Post-production longevity.*—Plants of the new Poinsettia maintain good substance and bract color for about four weeks under interior conditions.

*Inflorescence size.*—Diameter: About 13 cm. Height (depth): About 7 cm.

*Flower bracts.*—Quantity per inflorescence: About 30. Length, largest bracts: About 8 cm. Width, largest bracts: About 8.5 cm. Shape: Roughly ovate. Apex: Acuminate. Base: Obtuse. Margin: Entire. Texture, upper and lower surfaces: Glabrous; velvety. Surface: Rugose. Orientation: Recurved. Venation pattern: Pinnate. Color: Developing or transitional bracts, upper surface: 10C. Developing or transitional bracts, lower surface: 10D. Fully developed bracts, upper and lower surfaces: 10D; color does not fade with subsequent development. Venation, upper and lower surfaces: 10D. Bract petiole: Length: About 1.2 cm. Diameter: About 3 mm. Texture, upper and lower surfaces: Smooth; glabrous. Color: 145A.

*Cyathia.*—Quantity: About 26 per corymb. Diameter of cyathia cluster: About 3 by 3.5 cm. Length: About 1 cm. Width: About 5 mm. Shape: Ovoid. Color: Immature: 144C. Mature: 144B. Peduncle: Length: About 2.5 mm. Diameter: About 2 mm. Strength: Strong. Aspect: Mostly upright to slightly outward. Texture: Smooth; glabrous. Color: 144C. Stamens: Quantity per cyathium: At least 20. Anther shape: Oval. Anther length: Less than 1 mm. Anther color: 4A. Amount of pollen: Scarce. Pollen color: 10A. Pistils: Quantity per cyathium: One. Pistil length: About 1.2 cm. Style length: About 2 mm. Style color: 145B. Stigma shape: Three-parted. Stigma color: 145B. Ovary color: 144B. Nectaries: Quantity per cyathium: One. Size: About 3 mm by 4 mm. Color: 17A.

Disease/pest resistance: Resistance to pathogens and pests common to Poinsettias has not been observed on plants grown under commercial conditions.

It is claimed:

1. A new and distinct cultivar of Poinsettia plant named 'Eckaimon', as illustrated and described.

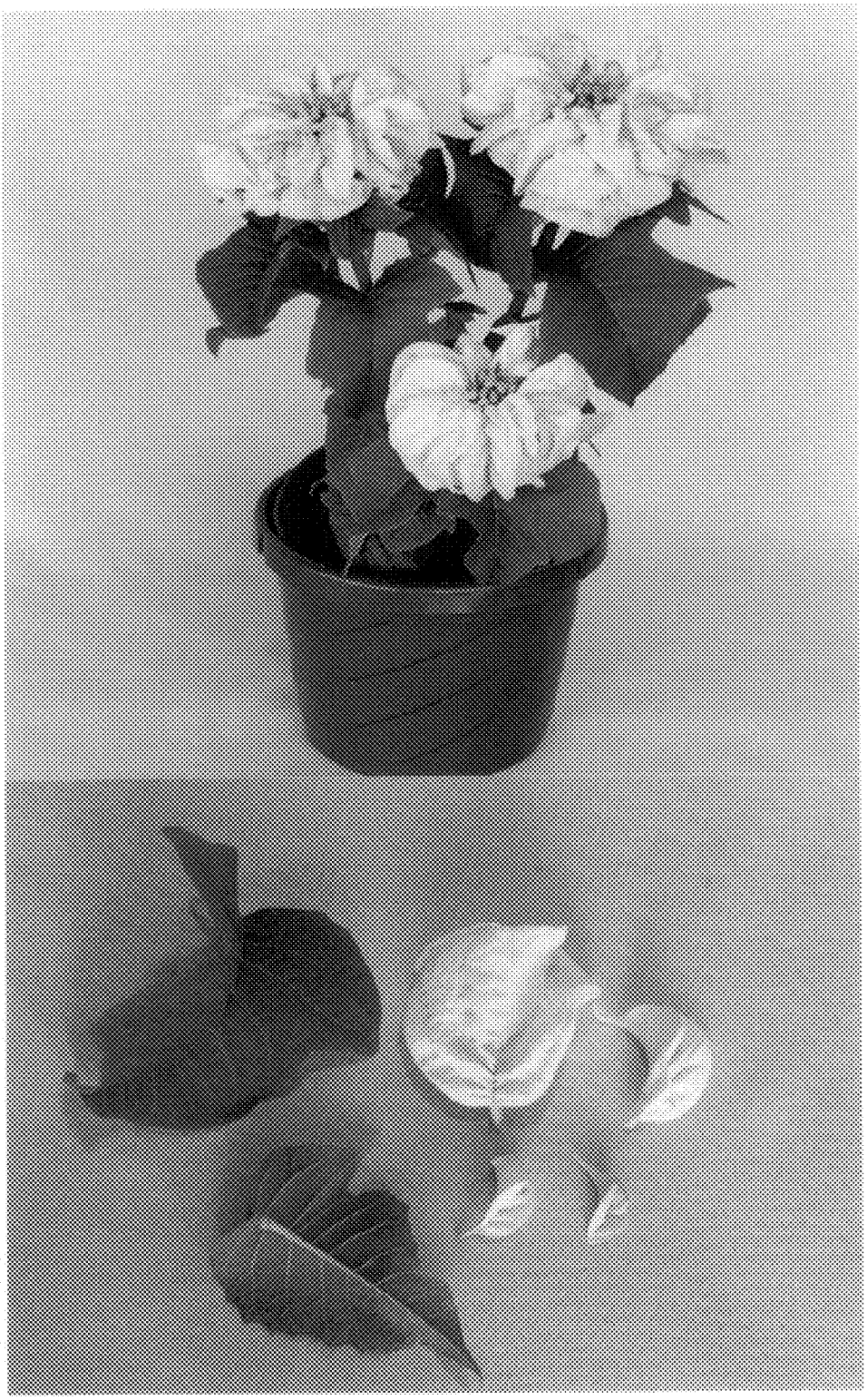

* * * * *